(12) United States Patent
Ujiie et al.

(10) Patent No.: US 8,951,621 B2
(45) Date of Patent: Feb. 10, 2015

(54) ROLL BODY OF BAND-LIKE PATCH

(75) Inventors: Takashi Ujiie, Osaka (JP); Kouji Kamata, Osaka (JP); Junya Nishimura, Osaka (JP); Tatsumi Ishikawa, Osaka (JP)

(73) Assignee: Nitto Denko Corporation, Osaka (JP)

( * ) Notice: Subject to any disclaimer, the term of this patent is extended or adjusted under 35 U.S.C. 154(b) by 67 days.

(21) Appl. No.: 13/562,617

(22) Filed: Jul. 31, 2012

(65) Prior Publication Data

US 2013/0034677 A1  Feb. 7, 2013

(30) Foreign Application Priority Data

Aug. 1, 2011 (JP) .................. 2011-168470
Jan. 12, 2012 (JP) .................. 2012-000114
Feb. 21, 2012 (JP) .................. 2012-035590

(51) Int. Cl.
| | | |
|---|---|---|
| B32B 9/00 | (2006.01) | |
| B32B 33/00 | (2006.01) | |
| A61F 15/00 | (2006.01) | |
| A61F 13/02 | (2006.01) | |
| B65D 63/10 | (2006.01) | |
| C09J 7/04 | (2006.01) | |

(52) U.S. Cl.
CPC ........... A61F 15/002 (2013.01); A61F 13/0273 (2013.01); A61F 13/0269 (2013.01); B65D 63/1009 (2013.01); C09J 7/047 (2013.01); C09J 2201/606 (2013.01); C09J 2433/00 (2013.01); Y10S 428/906 (2013.01)
USPC .......................... 428/40.1; 428/41.8; 428/906

(58) Field of Classification Search
CPC ..... A61F 13/0269; A61F 13/58; A61F 13/60; A61F 13/581; A61F 13/02; A61F 15/002; C09J 7/0232; C09J 7/02; C09J 7/0207; C09J 7/04
USPC ............................... 428/40.1, 41.8, 42.1, 906
See application file for complete search history.

(56) References Cited

U.S. PATENT DOCUMENTS 4,801,480 A * 1/1989 Panza et al. ................. 428/41.9
2011/0098622 A1* 4/2011 Hatanaka et al. ............ 602/52

FOREIGN PATENT DOCUMENTS

| EP | 0 148 587 A2 | 7/1985 |
| EP | 2 050 801 A1 | 4/2009 |

(Continued)

OTHER PUBLICATIONS

Nitto Denko Corporation, "http://ntmed.co.jp/medical/index.html", Retrieved Jun. 26, 2012, 2 pages total.

(Continued)

*Primary Examiner* — Patricia L Nordmeyer
(74) *Attorney, Agent, or Firm* — Sughrue Mion, PLLC

(57) ABSTRACT

Provided is a roll body of a band-like patch that can be held in a roll-like form without causing deviated rolling or unrolling, and can allow simple pulling out of a patch without causing stickiness on a person's hand or fingers when being pulled out. In the roll body of a band-like patch formed by rolling a band-like patch including a cloth support, a pressure-sensitive adhesive layer, and a release liner laminated in this order, at least one temporary attachment region in which a temporary attachment layer is formed and at least one grip region in which no temporary attachment layer is formed are provided at an interface between a back face of the cloth support and a back face of the release liner.

10 Claims, 6 Drawing Sheets

(56) References Cited

FOREIGN PATENT DOCUMENTS

| | | | |
|---|---|---|---|
| GB | 1293797 A | * | 10/1972 |
| JP | 54-84356 A | | 6/1979 |
| JP | 3-107464 U | | 11/1991 |
| JP | 7-6252 U | | 1/1995 |
| JP | 9-53058 A | | 2/1997 |

OTHER PUBLICATIONS

Nitto Denko Corporation, "http://ntmed.co.jp/taping/index.html", Retrieved Jun. 26, 2012, 2 pages total.

Extended European Search Report, dated Oct. 28, 2013, issued by the European Patent Office in counterpart European Application No. 12178767.5.

* cited by examiner

ROLL BODY OF BAND-LIKE PATCH

FIELD OF THE INVENTION

The present invention relates to a roll body obtained by rolling a band-like patch in which a cloth support, a pressure-sensitive adhesive layer, and a release liner are laminated, and which is used in a medical and sanitary field, a sports field, or the like for taping treatment, sports taping, or the like.

BACKGROUND OF THE INVENTION

Skin patches conventionally used in a medical and sanitary field, a sports field, or the like are attached on or rolled around a person's skin, thereby exhibiting the effects of medical treatment for a target part, prevention of injury, or the like (Non-Patent Literature Documents 1 and 2).

As such skin patches, there are two kinds of skin patches including a skin patch in which a pressure-sensitive adhesive layer is formed on one face of a support and that has no release liner, and a skin patch in which the pressure-sensitive adhesive layer is formed on one face of the support and the release liner is pasted so as to cover the pressure-sensitive adhesive layer, and both of these are rolled around a rolling core or the like and provided as roll-like products.

Among the above skin patches, the former skin patch that has no release liner can be obtained as a roll-like skin patch without deviated rolling by performing rolling while the pressure-sensitive adhesive layer formed on the support is bonded to the face (hereinafter referred to as the back face of the support) of the support opposite to the pressure-sensitive adhesive layer. However, since there is no release liner that covers the pressure-sensitive adhesive layer, there has been a possibility that, when the skin patch is pulled out during use, a person's hands, fingers, or the like come into direct contact with and become soiled by the pressure-sensitive adhesive layer, or the fats on the person's hands, fingers, or the like may adhere to the pressure-sensitive adhesive layer, which results in a decrease in adhesive force. Additionally, in the skin patch that has no release liner, generally, release treatment is performed on the back face of the support so that the skin patch is easily pulled out. However, there are problems in that writing or printing for performing marking or the like is difficult on the back face of the support subjected to such release treatment, or peeling-off is apt to occur if the skin patch is overlappingly pasted.

On the other hand, in order to solve the above problems, generally, the latter skin patch that has the release liner has been known. That is, in such a skin patch that has the release liner, the pressure-sensitive adhesive layer is covered with the release liner. Therefore, even if the skin patch is pulled out during use, there is no concern that a person's hands, fingers, or the like may come into direct contact with and become soiled by the pressure-sensitive adhesive layer, or the adhesive force of the pressure-sensitive adhesive layer may decrease. Additionally, since it is not necessary to perform the release treatment on the back face of the support, writing or printing can be performed on the back face of the support, and there is no concern that peeling-off may occur even if the skin patch is overlappingly pasted. However, since slippage over the back face of the support that comes into contact with the release liner occurs easily if the skin patch having the release liner is rolled into a roll, there is a problem in that deviated rolling, unrolling, or the like occurs and it is difficult to hold a roll-like form.

In order to solve such problems, there is disclosed a single face pressure-sensitive adhesive tape provided with release sheet as described in Patent Document 1, in which one face of a single-face release sheet subjected to easy-release treatment is joined to a tape support via pressure-sensitive adhesive, and the other face of the single-face release sheet that is not subjected to easy-release treatment is formed with a resin layer having the property of being stuck to the tape support in a re-releasable manner. However, since resin having a sticking property is present in the release sheet, the release sheet easily sticks on a person's hand or fingers during use, and may be hard to use. Additionally, in a case where the pressure-sensitive adhesive tape with a release sheet in which the above-mentioned resin layer is formed on the whole surface of the release sheet is rolled while the release sheet comes into contact with the tape support, even if an attempt is made to pull out the pressure-sensitive adhesive tape, there is a problem in that a staring point for pulling-out cannot be obtained, and the pressure-sensitive adhesive tape is not easily pulled out.

Additionally, Patent Document 2 discloses that a slightly pressure-sensitive adhesive face is provided on the hack face of a release material, or pressure-sensitive adhesive is provided in the shape of a line or a dot. However, since a material having a pressure-sensitive adhesiveness is formed on the back face of the release material, there is a problem in that the back face of the release material sticks on a person's hand or fingers during use and it is hard to use.

Moreover, a finishing end edge that is a rolling stop portion of the roll body of the band-like patch formed by rolling is apt to be loosened, and a method of performing fixing using a pressure-sensitive adhesive tape or the like so that the finishing end edge is not loosened is used (refer to Patent Document 3).

However, in the method using a pressure-sensitive adhesive tape, the extra work of cutting the pressure-sensitive adhesive tape to a desired size or attaching the cut pressure-sensitive adhesive tape on the finishing end edge of the roll body is required. Since such a pressure-sensitive adhesive tape is peeled when the band-like patch is used and is discarded as trash after peeling, this is not environmentally preferable.

Generally, when the band-like patch in which the support, the pressure-sensitive adhesive layer, and the release liner are laminated is rolled around the rolling core, it is necessary to fix a starting end edge of the band-like patch at the beginning of rolling to the rolling core so that the band-like patch does not slip off the rolling core. As methods of fixing the starting end edge of the band-like patch to the rolling core, there is a method (refer to Patent Document 4) of fixing the starting end edge of the band-like patch, using an article in which a pressure-sensitive adhesive layer is formed in advance on the whole surface of the rolling core, or a method (refer to Patent Document 3) of fixing the starting end edge of the band-like patch to the rolling core, using a pressure-sensitive adhesive tape.

However, in the method of using an article in which a pressure-sensitive adhesive layer is formed in advance on the whole surface of the rolling core, a pressure-sensitive adhesiveness is given to the surface of the rolling core itself. Therefore, there is a case where the surface of the rolling core having a pressure-sensitive adhesiveness sticks on a worker's hands, fingers, or the like, and the workability when the rolling core is handled becomes worse. Additionally, if the article in which the pressure-sensitive adhesive layer is formed on the whole surface of the rolling core is kept as it is, there is a possibility of dust or the like sticking on the pressure-sensitive adhesive layer formed on the whole surface of the rolling core during storage, and the article being not good sanitarily.

On the other hand, in the method using a pressure-sensitive adhesive tape, if the band-like patch is rolled into a roll after being fixed to the rolling core by attaching the pressure-sensitive adhesive tape, there is a case where the patch in the vicinity of the rolling core deforms (takes on an unwanted appearance) in the shape of the pressure-sensitive adhesive tape attached and a patch with poor appearance is obtained. Additionally, in order to fix the starting end edge of the band-like patch to the rolling core using the pressure-sensitive adhesive tape, extra work of cutting the pressure-sensitive adhesive tape to a proper length and attaching the cut pressure-sensitive adhesive tape on the starting end edge of the patch and the rolling core is required.

Patent Document 1: JP-A-9-53058
Patent Document 2: JP-UM-54-84356
Patent Document 3: JP-UM-7-6252
Patent Document 4: JP-UM-3-107464
Non-Patent Document 1: http://ntmed.co.jp/taping/index.html
Non-Patent Document 2: http://ntmed.co.jp/medical/index.html

SUMMARY OF THE INVENTION

An object of the invention is to provide a roll body obtained by rolling a band-like patch, in which a pressure-sensitive adhesive layer and a release liner are laminated on a support, which can be held in a roll-like form without causing deviated rolling or unrolling, and can allow easy pulling out of a patch without causing stickiness on a person's hand or fingers when being pulled out.

The invention has been thoroughly investigated and elucidated in order to solve the above problems and is as shown below.

(1) A roll body of a band-like patch formed by rolling a band-like patch comprising a cloth support, a pressure-sensitive adhesive layer, and a release liner laminated in this order, wherein at least one temporary attachment region in which a temporary attachment layer is formed and at least one grip region in which no temporary attachment layer is formed are provided at an interface between a back face of the cloth support and a back face of the release liner.

(2) The roll body of a band-like patch according to item (1), wherein said temporary attachment region in which the temporary attachment layer is formed and said grip region in which no temporary attachment layer is formed are provided on the back face of the release liner.

(3) The roll body of a band-like patch according to item (1), wherein said grip regions are located at both width end edges of the band-like patch.

(4) The roll body of a band-like patch according to item (1), wherein said grip region is located at a finishing end edge of the band-like patch.

(5) The roll body of a band-like patch according to item (1), wherein said temporary attachment layer exposed after pulling out the band-like patch from the roll body has substantially no surface tackiness.

(6) The roll body of a band-like patch according to item (1), wherein said temporary attachment layer is constituted of a hot melt material.

(7) The roll body of a band-like patch according to item (1), wherein a shape of said temporary attachment layer is dotted, grid-like, or linear along the longitudinal direction of the band-like patch.

(8) The roll body of a band-like patch according to item (1), wherein said temporary attachment region is substantially line-symmetric with respect to the center of width of the band-like patch.

(9) The roll body of a band-like patch according to item (1), further comprising a rolling core around which the band-like patch is rolled, and a bonding layer provided between the rolling core and the band-like patch.

(10) The roll body of a band-like patch according to item (9), wherein a planar shape of the bonding layer is a substantially rectangular shape formed by a length (W) of the bonding layer in the width direction of the surface of the rolling core and a length (L) of the bonding layer in the rolling direction of the surface of the rolling core, and wherein a length (W) of the bonding layer in the width direction of the surface of the rolling core is a length that is 50% to 100% of a total width ($W_0$) of the surface of the rolling core, and a length (L) of the bonding layer in the rolling direction of the surface of the rolling core is a length that is 3 mm or more and that is 1 to 100% of a total circumferential length ($L_0$) of the surface of the rolling core in the rolling direction.

The invention relates to a roll body of a band-like patch formed by rolling a band-like patch including a cloth support, a pressure-sensitive adhesive layer, and a release liner. A temporary attachment region(s) in which a temporary attachment layer is formed and a grip region in which no temporary attachment layer is formed are provided at an interface between a back face (the face of the cloth support opposite to the pressure-sensitive adhesive layer laminated face) of the cloth support and a back face (the face of the release liner opposite to the pressure-sensitive adhesive layer laminated face) of the release liner. In the roll body of the band-like patch of the invention, the band-like patch is rolled while the back face of the cloth support and the back face of the release liner are bonded via the temporary attachment layer. This provides effects that sideslip is suppressed and deviated rolling is prevented, and unrolling is prevented so that a roll-like form can be kept.

In order to prevent the deviated rolling when the band-like patch is rolled, it is important to form the temporary attachment layer as described above. However, in the roll body of the band-like patch of the invention, if the temporary attachment layer is formed at the whole interface between the back face of the cloth support and the back face of the release liner, the whole back face of the release liner comes to be bonded to the whole back face of the cloth support via the temporary attachment layer, so that problems occur in that a starting point for pulling out the patch cannot be obtained, and it is difficult to grip and pull out the patch with a person's hand or fingers.

For this reason, the roll body of the band-like patch of the invention has a feature that the grip region formed with no temporary attachment layer is provided at the interface between the back face of the cloth support and the back face of the release liner so that the patch can be easily pulled out. The grip region formed with no temporary attachment layer serves as a starting point when the patch is pulled out from the roll body of the band-like patch of the invention, and the patch can be simply pulled out by gripping the grip region with a person's hand or fingers.

Figure 1:
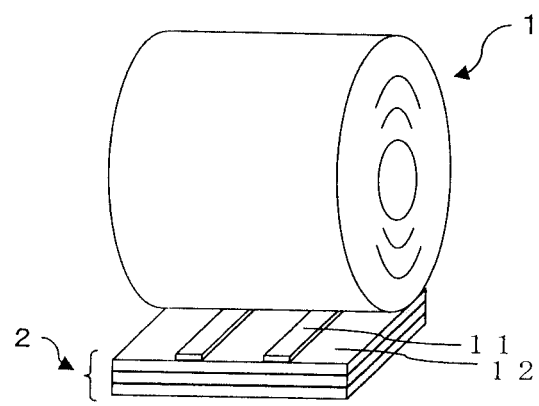
FIG. 1 is a perspective view showing an embodiment of a roll body of a band-like patch of the invention.

In addition, in order to describe the concept of the invention plainly, respective constituent elements are drawn in an enlarged manner in all the drawings. Hatchings in the drawings are appropriately added so as to easily distinguish the respective constituent elements from each other.

DETAILED DESCRIPTION OF THE INVENTION

In a roll body of a band-like patch of the invention, in order to prevent deviated rolling or unrolling when the band-like patch is rolled, the interface between a back face of the cloth support and a back face of the release liner has a temporary attachment region(s) provided with a temporary attachment layer, and has a grip region(s) where no temporary attachment layer is provided so as to allow easy pulling out of the band-like patch.

Preferably, the temporary attachment layer in the invention is provided substantially and continuously along the longitudinal direction of the band-like patch. Since such a temporary attachment layer is provided, when the band-like patch is rolled again in the shape of a roll after being pulled out, the band-like patch is lightly pressed via the temporary attachment layer, so that the back face of the cloth support and the back face of the release liner can be bonded. Thus, the band-like patch can be simply and easily restored to a roll-like form.

Additionally, in the roll body of the band-like patch of the invention, preferably, a second temporary attachment layer is formed on the back face of the release liner or the back face of the cloth support in addition to the above temporary attachment layer, in a band-like patch having a finishing end edge of the roll body as a start point and having a ¼ circumferential length in a rolling direction in which the roll body is exposed as a terminal point. By pressing the band-like patch lightly via the second formed temporary attachment layer, the finishing end edge of the roll body can be simply and easily fixed and maintained in the form of a roll body, and the roll body of the band-like patch of the invention is obtained. As such, according to the invention, it is not necessary to use a pressure-sensitive adhesive tape for fixing the finishing end edge. Therefore, the work of attaching a pressure-sensitive adhesive tape can be omitted, and the workability for fixing the finishing end edge of the roll body is markedly improved. Additionally, since it is not necessary to use a pressure-sensitive adhesive tape, dust is not emitted, which is also advantageous in respect of the environment.

The second temporary attachment layer formed in the above-described place has a planar shape with a given area, in order to firmly fix the finishing end edge of the roll body and maintain the termination edge in the form of a roll body. That is, preferably, such second temporary attachment layer has a planar shape specified by the rolling direction length (L') and width (W') of the second temporary attachment layer, the length L' is 3 mm or more, and is 3% to 25% with respect to one circumferential length ($L_0'$) in the rolling direction in which the roll body is exposed, and the width W' is 10% to 100% of the total width ($W_0'$) of the roll body. Moreover, more preferably, the length L' is 3 mm or more and is 3% to 20% with respect to the length $L_0'$, and the width W' is 10% to 80% of the total width $W_0'$. In addition, in order to fix the band-like patch in a well-balanced manner in the right and left direction, preferably, the second temporary attachment layer is formed so as to become line-symmetric with respect to the center of width of the roll body.

Since the area of the temporary attachment layer is too small in a case where the width W' of the second temporary attachment layer is less than 10% with respect to the total width $W_0'$ of the roll body, there is a possibility that the band-like patch cannot be appropriately fixed depending on the case, and cannot be maintained in the form of a roll body. Similarly, even in a case where the length L' of the second temporary attachment layer is less than 3 mm, there is a possibility that the band-like patch cannot be appropriately fixed and cannot be maintained in the form of a roll body. On the other hand, if the length L of the second temporary attachment layer exceeds 25% (¼ circumferential length in the rolling direction) with respect to the length L', not only is this economically disadvantageous, but also, there is a possibility that the band-like patch is not easily pulled out from the form of the roll body at the time of using the band-like patch.

Figure 8:
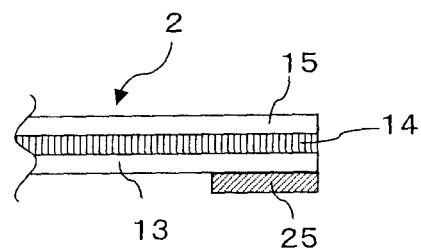
FIG. 8 is an enlarged lateral schematic view of an example of a laminated structure in the vicinity of a finishing end edge of the band-like patch.

A plurality of the second temporary attachment layers having such a planer shape may be formed. Additionally, although the second temporary attachment layer may be formed either on the back face of the cloth support or on the back face of the release liner that constitutes the band-like patch, since occurrence of problems concerns such as a possibility of the second temporary attachment layer being contaminated when the band-like patch is used if the second temporary attachment layer is formed on the back face of the cloth support, it is preferable that the second temporary patching layer be formed on the back face of the release liner as shown in FIG. 8.

Moreover, when the band-like patch is rolled, rolling can be made with either the cloth support or a release liner that constitutes the band-like patch being located outside, and position can be appropriately determined in consideration of applications, materials, or the like of the band-like patch. In addition, in a case where the second temporary attachment layer is formed on the back face of the release liner, it is more preferable to perform rolling with the cloth support being located outside in order to simplify the positioning when the second temporary attachment layer is formed.

In the invention, when the band-like patch is used, an embodiment in which no second temporary attachment layer is formed at the finishing end edge of the roll body is preferable in order to allow easy pulling out of the band-like patch from the roll body. Similarly, an embodiment in which no temporary attachment layer is formed at both end corners of the finishing end edge of the roll body is preferable. Moreover, an embodiment in which no second temporary attachment layer is formed at both width end edges of the roll body. In the roll body of the band-like patch of the invention, in such embodiment in which the second temporary attachment layer is not formed at such a position, a starting point when the band-like patch is pulled out can be obtained, and the band-like patch can be simply and easily pulled out by gripping the staring point.

Figure 9A:
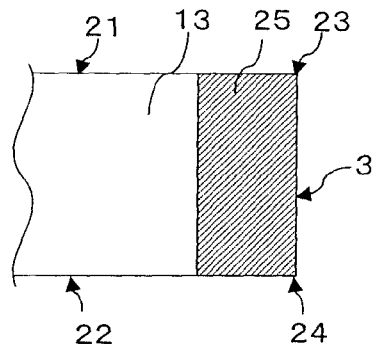
FIGS. 9A to 9D are views illustrating an embodiment of a second temporary attachment layer formed in the vicinity of the finishing end edge of the band-like patch, which are views showing a pattern drawn by the second temporary attachment layer when viewed from a release liner side of the band-like patch in a case where the second temporary attachment layer is formed on a back face of the release liner.
Figure 9B:
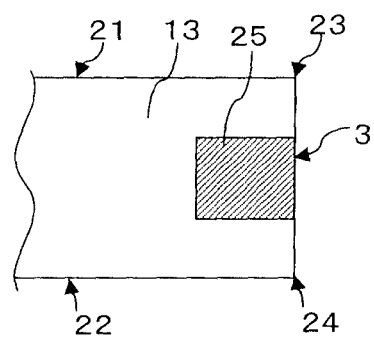
Figure 9C:
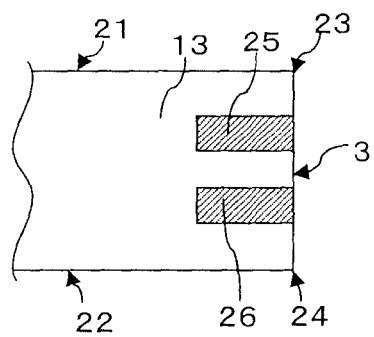
Figure 9D:
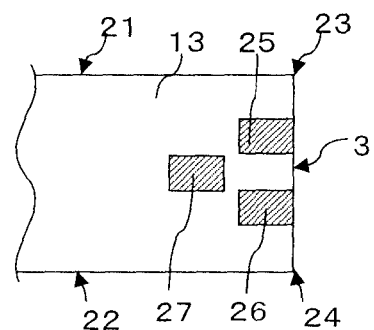

FIGS. 9A to 11D show embodiments of the second temporary attachment layer in the invention. FIG. 9A shows an embodiment in which the second temporary attachment layer is provided in the vicinity of all of the finishing end edge of the roll body, both the end corners of the finishing end edge, both the width end edges the finishing end edge. On the other hand, FIG. 9B, FIG. 9C, and FIG. 9D show embodiments in which the second temporary attachment layer is partially present at the finishing end edge of the roll body.

Moreover, FIGS. 10A to 11D all show embodiments in which the second temporary attachment layer is not provided at the finishing end edge of the roll body. When the band-like patch is pulled out from the roll body according to such embodiments in which the second temporary attachment layer is not provided at the finishing end edge, there is an advantage that pulling-out is easy.

In the embodiments of FIGS. 10A to 11D, preferably, the second temporary attachment layer is formed so that the shortest distance from the finishing end edge of the roll body to the second temporary attachment layer is 1 mm to 20 mm. Since the starting point for gripping is small in a case where the shortest distance from the finishing end edge of the roll body to the second temporary attachment layer is less than 1 mm, gripping becomes difficult when the band-like patch is pulled. Additionally, in a case where the shortest distance from the finishing end edge of the roll body to the second temporary attachment layer exceeds 20 mm, the finishing end edge of the band-like patch cannot be fixed to the roll body. Therefore, there is a possibility that handling may be difficult during storage, and the band-like patch itself may be damaged due to the finishing end edge that cannot be fixed to the roll body.

Although the planar shape of the second temporary attachment layer is not particularly limited like a substantially rectangular shape as shown in FIGS. 9A to 10D, a wavelike shape as shown in FIGS. 11A to 11D, or the like, the substantially rectangular shape is preferable if the point that the second temporary attachment layer can be easily and simply formed is taken into consideration.

Preferably, the temporary attachment layer and the second temporary attachment layer in the invention have a property with substantially no surface tackiness after the patch is pulled out from the roll body of the band-like patch. The property of substantially no surface tackiness in the invention means a property with no pressure-sensitive adhesiveness at room temperature, unlike a so-called pressure-sensitive adhesive.

Although the temporary attachment layer and the second temporary attachment layer show the property with no surface tackiness at room temperature, these layers have a property of flowability, and melting and deforming, due to heating. The temporary attachment layer and the second temporary attachment layer having such a property are, for example, formed on the back face of the release liner by heating and melting, and immediately rolled in the shape of a roll while being bonded with the back face of the cloth support, so that the roll body of the band-like patch of the invention with no deviated rolling can be obtained.

Moreover, since the temporary attachment layer and the second temporary attachment layer are formed on the back face of the release liner that is released and discarded when being used, neither the temporary attachment layer nor the second temporary attachment layer is present in the patch during wear, and there is no possibility that problems, such as drop-out of the temporary attachment layer or the second temporary attachment layer during wear, may occur. Additionally, in the roll body of the band-like patch of the invention, when the band-like patch is rolled so that the back face of the cloth support in which neither the temporary attachment layer nor the second temporary attachment layer is formed is located outside, the temporary attachment layer or the second temporary attachment layer formed on the back face of the release liner is not exposed to the outside of the roll body, and there is also no concern about occurrence of such a problem, for example, that the temporary attachment layer or the second temporary attachment layer become worn out, released, or drop out.

As the materials used for the temporary attachment layer and the second temporary attachment layer, those having no surface tackiness at room temperature, showing characteristics having flowability due to heating, and showing characteristics having excellent adhesive performance with the back face of the release liner are preferably used.

The materials showing such characteristics include hot melt materials. In more detail, one or two kinds of hot melt materials are used, which are selected from the group consisting of rubber-based materials, acrylic-based materials, polyolefin-based materials, polyurethane-based materials, polyamide-based materials, and ethylene vinyl acetate-based materials. Among these, rubber-based hot melt materials are preferably used. As the rubber-based hot melt materials, styrene-based hot melt materials, containing a base polymer composed mainly of one or two kinds of components selected from the group consisting of a styrene isoprene block copolymer, a styrene butadiene block copolymer, a styrene ethylene butylene block copolymer, and a styrene ethylene propylene block copolymer, are more preferably used because these materials have substantially no surface tackiness at room temperature, and easily flow due to heating.

The softening point of the hot melt materials is normally 60 to 180° C., and preferably 80 to 150° C. The hot melt materials whose softening point exceeds 180° C. require a special heating device for being heating and melted, and are not practical. Additionally, since the hot melt materials whose softening point is lower than 60° C. tend to have a pressure-sensitive adhesiveness at room temperature, these materials may be hard to use when being used such that the temporary attachment layer is sticky.

In a case where the temporary attachment layer (and the second temporary attachment layer) is (are) formed on the back face of the release liner, the thickness thereof is set to a suitable range in consideration of the performance of adhesion to the back face of the cloth support when being rolled in the shape of a roll, rolling the band-like patch without any deviated rolling, or the like. That is, the thickness of the temporary attachment layer (and the second temporary attachment layer) is (are) preferably 1 µm to 80 µm, and more preferably, 10 µm to 50 µm. Since sufficient adhesive performance with the back face of the cloth support is not obtained if the thickness of the temporary attachment layer (and the second temporary attachment layer) is (are) less than 1 µm, there is a possibility that unrolling may occur and the roll-like forming may not be held. On the other hand, since a large thickness difference occurs between the temporary attachment region and the grip regions if the thickness of the temporary attachment layer (and the second temporary attachment) layer exceeds (exceed) 80 µm, the possibility that the deviated rolling may occur becomes high. Moreover, depending on the kind and thickness of cloth supports that constitute the band-like patch, irregularities may be generated on the surface of the patch, and unwanted appearance may occur. In addition, since the second temporary attachment layer used in the invention tends to deform due to pressure unlike a general pressure-sensitive adhesive tape used in order to fix the finishing end edge of the band-like patch in the related art, even if the thickness of the second temporary attachment layer is a little large, deformation (unwanted appearance) of the patch by the second temporary attachment layer rarely occur.

Preferably, the width of the temporary attachment layer formed on the back face of the release liner is appropriately set so as to have grip regions at the width end edges of the band-like patch. Additionally, the thickness of the temporary attachment layer and the width of the temporary attachment layer can be appropriately set depending on the characteristics of materials that constitute the temporary attachment layer.

Preferably, the grip regions in the invention are located at both the width end edges of the band-like patch. Additionally, it is preferable that the grip region in the invention be located at the finishing end edge of the band-like patch. Since the band-like patch can be pulled out by gripping the grip regions with a person's hand or fingers owing to the presence of the grip regions in the band-like patch, handleability is markedly improved. On the other hand, in a case where the temporary attachment layer is formed on the whole release liner back face that constitutes the patch and no grip region is present, the whole back face of the release liner and the whole back face of the cloth support adhere to each other via the temporary attachment layer. Therefore, even if pulling out of the patch is attempted when being used, a starting point for pulling out the patch is not obtained, and it becomes difficult to easily pull out the patch.

In order to provide grip regions with sizes sufficient to grip the patch with a person's hands, fingers, or the like, it is preferable to set the grip regions where no temporary attachment layer is formed at least in regions of less than 5 mm from each width end edge of the band-like patch. Since the grip regions for gripping the patch with a person's hand or fingers become narrow if the temporary attachment layer is formed in the regions of less than 5 mm from each width end edge of the band-like patch, the patch is not easily pulled out and is hard to use.

Preferably, the coating shape of the temporary attachment layer is dotted, grid-like, or linear along the longitudinal direction of the band-like patch. The linear coating shape means a coating shape including continuous lines having a specific width, such as a straight line, a curved line, and a wavy line, or a discontinuous line. In addition, it is more preferable that the coating shape of the temporary attachment layer be straight along the longitudinal direction of the band-like patch from the viewpoint that the temporary attachment layer can be easily formed.

Preferably, a formation region for the temporary attachment layer is substantially line-symmetric with respect to the center of width of the band-like patch in order to prevent the deviated rolling when the band-like patch is rolled. If the band-like patch in which the formation region for the temporary attachment layer is deviated from a substantial line-symmetric state with respect to the center of width of the band-like patch is rolled in the shape of a roll, the band-like patch may be rolled in the shape of a so-called bamboo shoot, and there is a possibility that deviated rolling may occur. In addition, the case where there is deviation from the line symmetry according to the invention means a case where there is a deviation of 10% or more with respect to the length of the band-like patch in the width direction.

The roll body of the band-like patch of the invention may be obtained by rolling the band-like patch around the rolling core. In this case, it is preferable to provide a bonding layer between the band-like patch and the rolling core so that the band-like patch can be fixed to and rolled around the rolling core without slipping off when being rolled around the rolling core. The roll body of the band-like patch is obtained by simply and easily fixing and rolling the band-like patch to the rolling core via the bonding layer formed between the patch and the rolling core.

The starting end edge of the band-like patch can be simply and easily fixed to the rolling core by lightly pressing the starting end edge of the band-like patch against the rolling core via the bonding layer after the bonding layer is formed between the rolling core and the band-like patch immediately before the band-like patch is rolled around the rolling core. Thereby, the work of attaching a pressure-sensitive adhesive tape can be omitted, and the workability for fixing the band-like patch to the rolling core is markedly improved. Additionally, not only the work itself of attaching a pressure-sensitive adhesive tape can be omitted, but also there is no case that the band-like patch in the vicinity of the rolling core deforms (takes an unwanted appearance) like a case where a pressure-sensitive adhesive tape sticks and is fixed to the rolling core, the roll body of the band-like patch with pleasing appearance can be obtained. Moreover, since subtle alignment between the rolling core and the band-like patch can be simply performed when the starting end edge of the band-like patch is fixed to the rolling core, the patching deviation when the band-like patch is fixed to the rolling core can be prevented. Since no bonding layer is formed until just before the band-like patch is rolled around the rolling core, there is no possibility that dust may adhere when the rolling core is stored or that dust may stick on a worker's hands, fingers, or the like. Thus, the workability when the rolling core is handled is markedly excellent.

As the materials used for the bonding layer of the invention, materials that show characteristics having flowability due to heating or pressing and show characteristics having excellent adhesive performance with the rolling core or the patch are favorably used. As the materials that show such characteristics, materials same as those used for the temporary attachment layer and the second temporary attachment layer are preferably used.

The thickness of the bonding layer is set to a suitable range from the viewpoints of performance of adhesion to the rolling core or the patch or prevention of deformation (unwanted appearance) of the patch by the bonding layer. That is, the thickness of the bonding layer is preferably 1 µM to 40 µm, and more preferably, 2 µm to 30 µm. If the thickness of the bonding layer is less than 1 µm, there is a possibility that performance of adhesion to the rolling core or the patch may not be enough, and fixing may not be achieved. On the other hand, if the thickness of the bonding layer exceeds 40 µm, depending on the kind and thickness of cloth supports that constitute the patch, irregularities may be generated on the surface of the patch, and the unwanted appearance may occur. In addition, since the bonding layer used in the invention deforms due to pressure unlike a general pressure-sensitive adhesive tape that is a laminate of a substrate and a pressure-sensitive adhesive layer, even if the thickness of the bonding layer is a little large, deformation (unwanted appearance) of the patch by the bonding layer rarely occur.

The bonding layer of the invention has a planar shape having a given area in order to firmly fix the band-like patch to the rolling core. That is, the planar shape of the bonding layer is a substantially rectangular shape formed by the length (W) of the bonding layer in the width direction of the surface of the rolling core and the length (L) of the bonding layer in the rolling direction of the surface of the rolling core. Preferably, the length (W) of the bonding layer in the width direction of the surface of the rolling core is a length that is 50% to 100% of the total width ($W_0$) of the surface of the rolling core, and the length (L) of the bonding layer in the rolling direction of the surface of the rolling core is a length that is 3 mm or more and that is 1 to 100% of the total circumferential length ($L_0$) of the surface of the rolling core in the rolling direction. Moreover, from the viewpoint that fine adjustment of a fixed position is simply and easily performed when the band-like patch is fixed to the rolling core, it is more preferable that the length (L) of the bonding layer in the rolling direction of the surface of the rolling core be a length that is 3 mm or more and that is 1 to 40% of the total circumferential length ($L_0$) of the surface of the rolling core in the rolling direction. A plurality of the bonding layers having such a planar shape may be formed on the surface of the rolling core.

Since the adhesion area is too small in a case where the length (W) of the bonding layer in the width direction of the surface of the rolling core is less than 50% with respect to the total width ($W_0$) of the surface of the rolling core, there is a possibility that the band-like patch cannot be appropriately fixed to the rolling core depending on circumstances. Similarly, even in a case where the length (L) of the bonding layer in the rolling direction of the surface of the rolling core is less than 3 mm, fixing cannot be appropriately made. On the other hand, since the bonding layer is formed beyond the total circumferential length of the surface of the rolling core in the rolling direction if the length (L) of the bonding layer in the rolling direction of the surface of the rolling core exceeds 100% with respect to the total circumferential length ($L_0$) of the surface of the rolling core in the rolling direction, this is economically disadvantageous.

Preferably, the bonding layer of the invention is formed immediately before the band-like patch is rolled around the rolling core. Although the bonding layer may be formed on the band-like patch or may be formed on the rolling core, it is more preferable to form the bonding layer on the rolling core from the viewpoint of workability.

Additionally, when the hand-like patch is fixed to be rolled around the rolling core after the bonding layer is formed on the rolling core, rolling can be made with either the cloth support or the release liner that constitutes the band-like patch being located outside, and position can be appropriately determined in consideration of applications, materials, or the like of the band-like patch.

The cloth support used in the invention includes woven cloth, knitted cloth, net cloth, nonwoven cloth, or the like, and is generally excellent in permeability and stretchability. Those subjected to water treatment to such a degree that the effects of the invention are not impaired can also be used for the cloth support. Incidentally, generally, since the surface irregularities of the cloth support are large compared to a film, the area of adhesion with the temporary attachment layer becomes large, and the adhesive performance between the cloth support and the temporary attachment layer is improved. As the adhesive performance between the cloth support and the temporary attachment layer is improved, the effects of suppressing sideslip and preventing deviated rolling of the roll-like skin patch can be exerted.

As the materials for the cloth support, for example, natural fiber, such as cotton, silk, and hemp, synthetic fiber, such as polyester, polyamide, acrylate resin, polyurethane, polyethylene, and polypropylene, semi-synthetic fiber, such as acetate fiber, regenerated fiber, such as rayon fiber and cuprammonium rayon fiber, can be used.

In a case where woven cloth, silk cloth, or net cloth among cloth supports is used, woven cloth, knitted cloth, or net cloth obtained by subjecting a material for a cloth support to special processing and independently knitting stretch yarn, textured yarn, or conjugated yarn to which stretchability is given or synthetic yarn having high stretchability, or woven cloth, knitted cloth, or net cloth obtained by mixing and knitting such synthetic yarn and fiber having low stretchability can be used. Additionally, as knitting methods, general methods, such as warp knitting including tricot knitting, raschel knitting, and milanese knitting and weft knitting including flat knitting and circular knitting. However, provided are methods having elasticity and stretchability that can favorably exhibit the effects of followability or fixability that is required for the materials used for a medical and sanitary field, a sports field, and the like.

Although it is preferable to appropriately determine the thickness of the cloth support depending on the material quality, applications, or the like, in a case where a cloth support made of fabric such as woven cloth or nonwoven cloth, paper, or the like is used, the thickness of the cloth support is preferably 50 to 500 µm and more preferably 100 to 300 µm. In addition, since it may be difficult to measure absolute thickness in a case where a cloth support made of fabric or paper is used, it is suitable to use a support whose basis weight is 8 to 200 g/m².

As the pressure-sensitive adhesives used for the pressure-sensitive adhesive layer in the invention, general pressure-sensitive adhesives used in skin patches of a medical and sanitary field, a sports field, and the like can be applied. Specifically, pressure-sensitive adhesives, such as a natural rubber-based pressure-sensitive adhesive, a synthetic rubber-based pressure-sensitive adhesive, an acrylic pressure-sensitive adhesive, a silicone-based pressure-sensitive adhesive, a vinyl ether-based pressure-sensitive adhesive, a vinyl ester-based pressure-sensitive adhesive, a polyester-based pressure-sensitive adhesive, and an urethane-based pressure-sensitive adhesive, can be used. These can be used independently or in combination of a plurality thereof. In a case where the pressure-sensitive adhesives are used in patches of a medical and sanitary field, a sports field, and the like, materials with little stimulus to the skin that is an object to be patched are favorably used.

The pressure-sensitive adhesive layer can be added with various additives if needed, in addition to the above pressure-sensitive adhesives. Examples of the additives may include a plasticizer, a crosslinking agent, a tackifier, an antioxidant, a heat-resistant stabilizer, a light stabilizer, an antistatic agent, lubricant, a nucleating agent, a flame retarder, a pigment, a dye, and an active pharmaceutical agent, and these additives may be contained independently or more than two in the pressure-sensitive adhesive layer.

Although the thickness of the pressure-sensitive adhesive layer can be appropriately selected depending on the kind of a site to be used or a pressure-sensitive adhesive, the thickness of the pressure-sensitive adhesive layer is preferably 10 μm to 300 μm and more preferably 20 μm to 200 μm. If the thickness of the pressure-sensitive adhesive layer is less than 10 μm, there is a possibility that the patch may be released during wear due to deficiency of adhesive force of a skin surface. On the other hand, if the thickness of the pressure-sensitive adhesive layer exceeds 300 μm, a pressure-sensitive adhesive may protrude from an end portion of the patch and paste contamination may occur.

As the coating shape of the pressure-sensitive adhesive layer, the pressure-sensitive adhesive layer may be provided on the whole surface of one face of the support or may be partially provided thereon. In a case where the pressure-sensitive adhesive layer is partially provided in order to improve permeability to reduce heat damage of a skin surface, a coating shape, such as a dot shape or a strip shape, is provided. In a case where the space between strips is provided on the pressure-sensitive adhesive layer, the coating shape may be any of a straight shape, a wavy shape, a mountain shape, a sawtooth shape, and the like. Generally, although it is preferable that the coating shape be a wavy shape due to the reason that there is little temporal change in the cross-sectional area of the space between strips, the coating shape can be appropriately determined depending on the characteristics of a pressure-sensitive adhesive to be used or the applications of the skin patch of the invention.

Although release liners that are generally used can be applied as the release liner used in the invention, if the performance of adhesion performance with the temporary attachment layer or economical efficiency are taken into consideration, it is preferable to use a release liner made of paper. Examples of the release liner made of paper may include those obtained by coating a release agent having release performance, such as a silicone resin or a fluororesin, on the surface of high-quality paper, glassine paper, or parchment paper. In addition, the temporary attachment layer formed on the release liner is formed on the face of the release liner that is not subjected to release treatment. Additionally, the adhesion force of the temporary attachment layer formed on the release liner is set such that an adhesion force to the back face of the release liner becomes higher than an adhesion force to the back face of the support so that the temporary attachment layer does not remain on a back face of the support when the patch is pulled out. Additionally, in a case where the release liner side of the band-like patch is fixed to the rolling core via the bonding layer, fixing can be firmly made by adopting a release liner subjected to single face release treatment and making the face of the release liner that is not subjected to the release treatment abut on the bonding layer.

The roll body of the band-like patch of the invention is made as follows for an example. A pressure-sensitive adhesive solution is coated on one face of a support and is dried to form a pressure-sensitive adhesive layer, a release liner is stuck so as to cover the pressure-sensitive adhesive layer, and then, original fabric rolled into a roll is obtained. Next, the original fabric rolled into a roll is paid out and slit with a product width. Thereafter, a temporary attachment layer is formed on the back face of the release liner, and rolling is made so that the support is located outside the roll shape. Thereby, a roll body of a band-like patch of the invention can be obtained.

The temporary attachment layer in the invention is formed, for example, by heating and melting a material that constitutes the temporary attachment layer at a temperature that is higher than or equal to a softening point, and then coating the melt material on the back face of the release liner of the band-like patch. Coating methods that are generally used can be used as the method of forming the temporary attachment layer on the back face of the release liner. Examples of the coating methods may include contact coating methods, such as slot coater coating and roll coater coating, or non-contact coating methods, such as spray coating and dot coating. In the invention, coating methods including the non-contact coating methods like spray coating are preferably used from the viewpoint of easiness and simplicity of coating.

Preferably, the band-like patch in which the temporary attachment layer is formed on the back face of the release liner is rolled after the temporary attachment layer is formed and before the temperature of the temporary attachment layer falls to room temperature in order to improve the adhesive performance between the back face of the support and the back face of the release liner via the temporary attachment layer. For this reason, preferably, the temporary attachment layer is formed immediately before the band-like patch is rolled into a roll-like form.

Additionally, a moderate tension may be applied to such a degree that the patch does not deform excessively when the band-like patch is rolled. By applying a moderate tension, for example, in the case of the roll body of the band-like patch using a cloth support for the support, the irregular shape of the back face of the cloth support and the temporary attachment layer can be adapted to each other, further preventing deviated rolling or unrolling caused by side slip.

Moreover, the roll body of the rolled-round band-like patch may be warmed and aged in a roll-like form. That is, by warming and aging the patch in a roll-like form, the temporary attachment layer can be adapted to irregularities of the back face of the cloth support, further preventing unrolling. Although conditions for the warming and aging are appropriately adjusted to such a degree that the characteristics of the band-like patch are not impaired, the warming and aging is performed, for example, on the temperature condition of 60° C. to 100° C.

EXAMPLES

Although examples of the invention will be shown below and will be specifically described, the invention is not limited thereto, and various applications can be made without departing from the technical spirit and scope of the invention.

Example 1

An acrylic pressure-sensitive adhesive solution was obtained by copolymerizing a monomer mixture of 95 parts by weight of 2-ethyl hexyl acrylate and 5 parts by weight of acrylic acid in ethyl acetate under an inert gas atmosphere. A pressure-sensitive adhesive layer was formed by coating the acrylic pressure-sensitive adhesive solution on a silicone treatment face of a release liner in which high-quality paper was subjected to silicone treatment so the thickness thereof after drying became 80 μm, and drying the pressure-sensitive adhesive solution at 120° C. for 3 minutes. A band-like patch having the configuration of a cloth support/pressure-sensitive adhesive layer/release liner was obtained by pasting, on this pressure-sensitive adhesive layer, a stretchable woven cloth as a cloth support knitted so that 75 deniers of polyester yarn is stretchable by smooth knitting.

A bonding layer made of a styrene-isoprene-styrene block copolymer resin-based hot melt material (Nittaito H-6789B made by Nitta Gelatin Inc. and having a softening point of 104° C.) was formed by spray coating on the surface of a rolling core of 25 mm in diameter and 50 mm in width so as to become a substantially rectangular shape of 25 μm in coating thickness, 10 mm in length (L) in the rolling direction, and 50 mm (100% to the total width) in length (W) in the width direction, and then, a starting end edge on the release liner side of the band-like patch cut with a width of 50 mm was fixed to the rolling core via the bonding layer so that the cloth support of the band-like patch was located outside. A roll body of a band-like patch of the invention as shown in FIG. 1 was obtained by continuously forming two temporary attachment layers made of a styrene-isoprene-styrene block copolymer resin-based hot melt material (Nittaito H-6789B made by Nitta Gelatin Inc. and having a softening point of 104° C.) and having a coating width of 5 mm and a coating thickness of 25 μm, in the shape of a straight line along the longitudinal direction by spray coating so that the centerline of each temporary attachment layer came to the positions of 15 mm from each width end edge of the back face of the release liner, respectively, when the band-like patch was rolled into a roll.

Example 2

Figure 2:
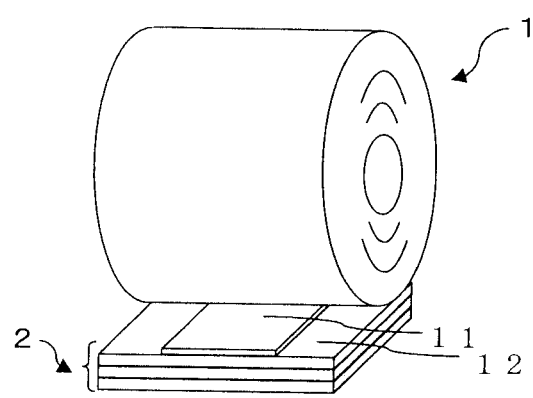
FIG. 2 is a perspective view showing another embodiment of the roll body of the band-like patch of the invention.
Figure 3:
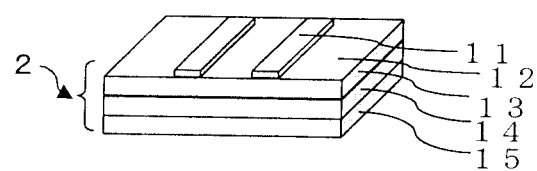
FIG. 3 is a perspective view of a patch cut out from the roll body of the band-like patch of the invention.
Figure 4:
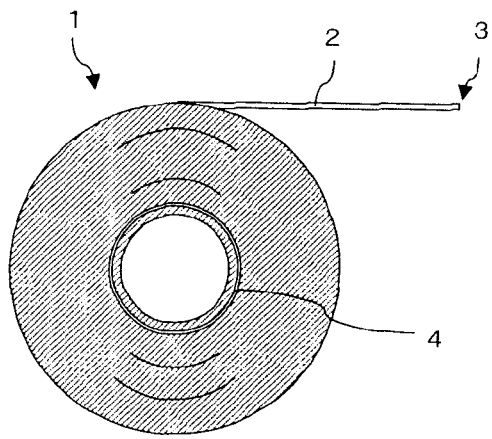
FIG. 4 is a lateral schematic view of a roll body of a band-like patch formed by rolling a band-like patch around a rolling core.
Figure 5:
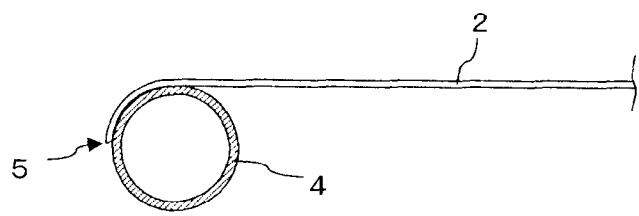
FIG. 5 is a lateral schematic view when a starting end edge of the band-like patch is fixed to the rolling core.
Figure 6:
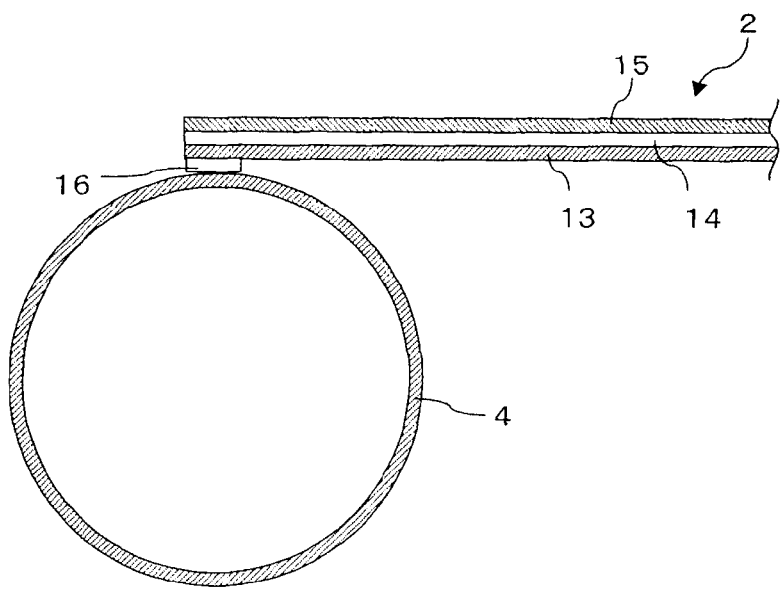
FIG. 6 is an enlarged lateral schematic view of FIG. 5.
Figure 7:
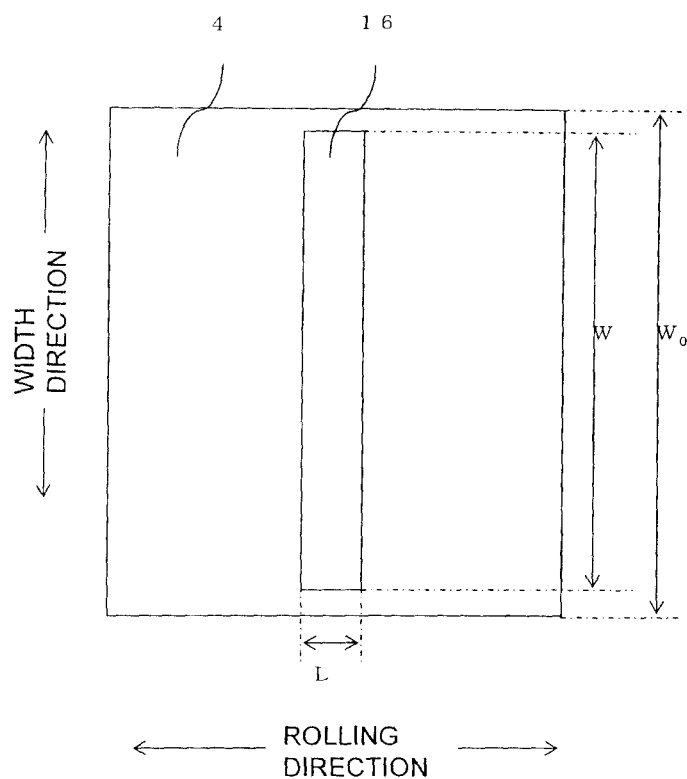
FIG. 7 is a front schematic view of the surface of the rolling core immediately after forming a bonding layer on the surface of the rolling core.

A roll body of a band-like patch of the invention as shown in FIG. 2 was obtained by the same method as Example 1 except that, in Example 1, one temporary attachment layer having a coating width 20 mm was provided so that the centerline of the temporary attachment layer came to the position of 25 mm from one width end edge on the back face of the release liner.

Example 3

A roll body of a band-like patch of the invention was obtained by the same method as Example 1 except that, in Example 1, two temporary attachment layers having a coating width 5 mm were provided so that the centerline of the temporary attachment layer came to the positions of 15 mm and 30 mm from one width end edge on the back face of the release liner.

Example 4

A bonding layer having a substantially rectangular shape of 25 μm in coating thickness, 10 mm in length (L) in the rolling direction, and 25 mm (100% to the total width) in length (W) in the width direction was formed by two-spot spray coating at an interval of 30 mm in length in the rolling direction on the surface of a rolling core of 25 mm in diameter and 25 mm in width, and then, a starting end edge on the release liner side of the band-like patch was fixed to the rolling core via the bonding layer so that the cloth support of the band-like patch cut with a width of 25 mm was located outside. A roll body of a band-like patch of the invention was obtained by continuously forming a temporary attachment layer having a coating width of 5 mm and a coating thickness of 25 μm, in the shape of a straight line along the longitudinal direction by spray coating so that the centerline of the temporary attachment layer came to the position of 12.5 mm from one width end edge of the back face of the release liner, respectively, when the band-like patch was rolled into a roll.

Example 5

A bonding layer having a substantially rectangular shape of 25 μm in coating thickness, 10 mm in length (L) in the rolling direction, and 150 mm (100% to the total width) in length (W) in the width direction was formed by two-spot spray coating at an interval of 30 mm in length in the rolling direction on the surface of a rolling core of 25 mm in diameter and 150 mm in width, and then, a starting end edge on the release liner side of the band-like patch was fixed to the rolling core via the bonding layer so that the cloth support of the band-like patch cut with a width of 150 mm was located outside. A roll body of a band-like patch of the invention was obtained by continuously forming two temporary attachment layers having a coating width of 5 mm and a coating thickness of 25 μm, in the shape of a straight line along the longitudinal direction by spray coating so that the centerline of each temporary attachment layer came to the position of 15 mm from each width end edge of the back face of the release liner, respectively, when the band-like patch was rolled into a roll.

Comparative Example 1

A roll body of a band-like patch was obtained by the same method as Example 1 except that, in Example 1, no temporary attachment layer was provided.

Comparative Example 2

A roll body of a band-like patch was obtained by the same method as Example 1 except that, in Example 1, a temporary attachment layer was provided on the whole back face of the release liner.

Comparative Example 3

A roll body of a band-like patch was obtained by the same method as Example 1 except that, in Example 1, a polyethylene film (25 μm in thickness) was used instead of the cloth support.

Example 6

Figure 10A:
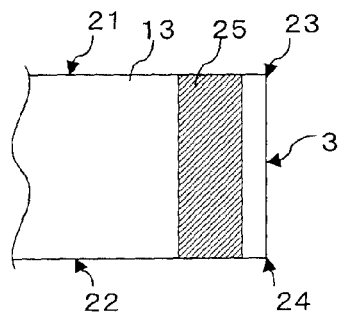
FIGS. 10A to 10D are views illustrating another embodiment of the second temporary attachment layer formed in the vicinity of the finishing end edge of the band-like patch, which are views showing a pattern drawn by the second temporary attachment layer when viewed from the release liner side of the band-like patch in a case where the second temporary attachment layer is formed on the back face of the release liner.
Figure 10B:
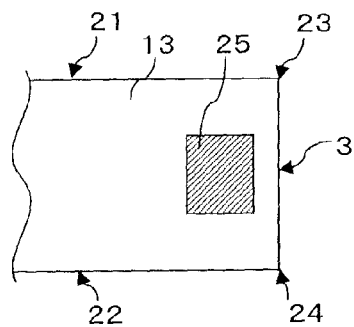
Figure 10C:
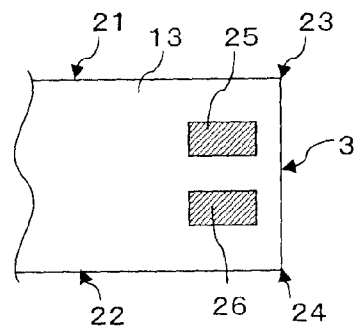
Figure 10D:
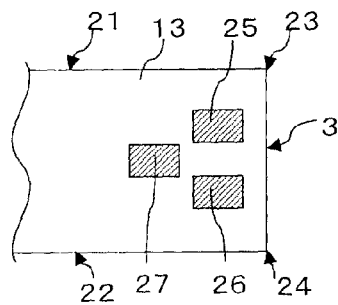
Figure 11A:
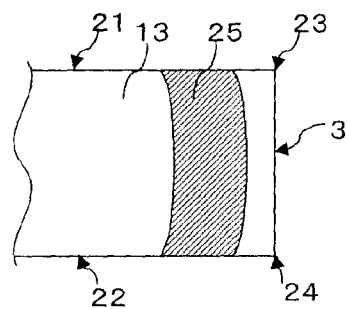
FIGS. 11A to 11D are views illustrating still another embodiment of the second temporary attachment layer formed in the vicinity of the finishing end edge of the band-like patch, which are views showing a pattern drawn by the second temporary attachment layer when viewed from the release liner side of the band-like patch in a case where the second temporary attachment layer is formed on the back face of the release liner.
Figure 11B:
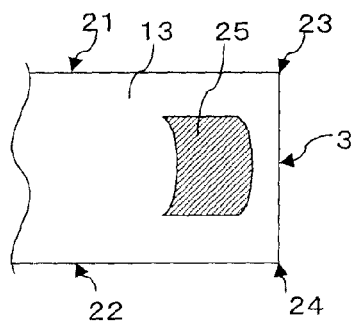
Figure 11C:
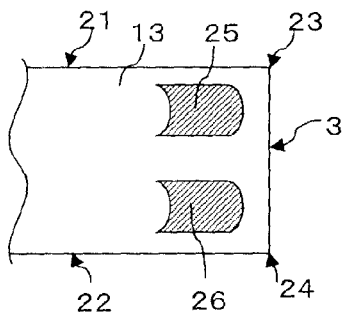
Figure 11D:
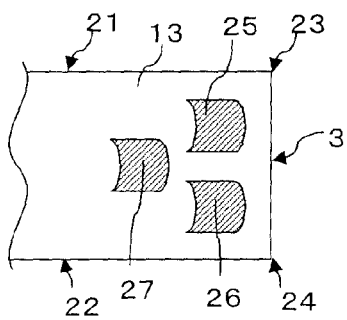

In the process of cutting the band-like patch of Example 1 with a width of 25 mm, then fixing the band-like patch to a rolling core of 25 mm in diameter and 25 mm in width so that the cloth base material was located outside, and then rolling the band-like patch into a roll, a roll body of a band-like patch of the invention was obtained by forming, on the back face of the release liner of the band-like patch, a second temporary attachment layer having a substantially rectangular shape of 25 μm in coating thickness, 10 mm in length in the rolling direction (5% with respect to one circumferential length in the rolling direction in which the roll body is exposed), and 10 mm (40% to the total width) in length line-symmetrically with respect to the center of the width as shown in FIG. 10B, using a styrene-isoprene-styrene block copolymer resin-based hot melt material (Nittaito H-6789B made by Nitta Gelatin Inc. and having a softening point of 104° C.) as the second temporary attachment layer, and then by cutting the band-like patch at a position 3 mm in a rolling stop direction apart from the formation end of the second temporary attachment layer, and simultaneously fixing the cut finishing end edge to the roll body.

Experimental Example 1

Evaluation of Deviated rolling and Unrolling

The form of the roll body after the band-like patch is rolled was determined visually. As for the determination of the deviated rolling, a case where the band-like patch after rolling deviated by 0% or more and less than 5% with respect to the width of band-like patch was determined as O, a case where the band-like patch deviated by 5% or more and less than 10% was determined as Δ, and a case where the band-like patch deviated by 10% or more was determined as X. Additionally, as the for the determination of the unrolling, a case where the finishing end edge of the roll body after rolling was fixed into a roll and there was no unrolling was determined as O, and a case where the fixing of the finishing end edge was insufficient and unrolling occurred was determined as X. The evaluation results are shown in Table 1.

Experimental Example 2

Evaluation of Operational Performance (Gripping Performance and Adhesiveness) and Appearance (Anchoring Damage of Temporary Attachment Layer)

The operational performance (gripping performance and the adhesiveness of the temporary attachment layer) when the patch was pulled out from the roll body of the band-like patch and the appearance (anchoring damage of the temporary attachment layer) after pulling-out were visually determined. As the determination of the operational performance (gripping performance), a case where the end edge of the patch was simply gripped was determined as O, and a case where the gripping was difficult was determined as X. Additionally, as for the determination of the operational performance (adhesiveness), a case where the adhesion force of the temporary attachment layer was suitable and the patch was easily pulled out was determined as O, a case where the adhesion force of the temporary attachment layer was strong and it was difficult to pull out the patch was determined as Δ, and a case where the adhesion force of the temporary attachment layer was weak, and the back face of the release liner and the back face of the cloth support was not sufficiently bonded via the temporary attachment layer was determined as X.

Moreover, as for the determination of the appearance (anchoring damage of the temporary attachment layer), a case where release (anchoring damage) of the temporary attachment layer did not occur when the patch was pulled from the roll body of the band-like patch was determined as O, and a case where release (anchoring damage) of the temporary attachment layer occurred and the temporary attachment layer adhered to the back face of the cloth support and the release liner back face, respectively, was determined as X. The evaluation results are shown in Table 1. In addition, since the article of Comparative Example 1 did not have the temporary attachment layer, the evaluation of the operational performance (adhesive performance) and the appearance (anchoring damage) were not performed.

TABLE 1

| Experiments | Contents | Examples | | | Comparative Examples | | |
|---|---|---|---|---|---|---|---|
| | | 1 | 2 | 3 | 1 | 2 | 3 |
| Experiment 1 | Deviated Rolling | O | O | Δ | X | O | X |
| | Unrolling | O | O | O | X | O | X |
| Experiment 2 | Operational Performance (Gripping Performance) | O | O | O | O | X | O |

TABLE 1-continued

| Experiments | Contents | Examples | | | Comparative Examples | | |
|---|---|---|---|---|---|---|---|
| | | 1 | 2 | 3 | 1 | 2 | 3 |
| | Operational Performance (Adhesiveness) | O | O | O | No Evaluation | Δ | X |
| | Appearance (Anchoring Damage) | O | O | O | No Evaluation | X | O |

It is clear from the results of the articles of Examples having the temporary attachment layer and the article of Comparative Example 1 in which no temporary attachment layer is present that the articles of the invention are a roll body of a band-like patch that is excellent in terms of deviated rolling and unrolling. Additionally, it is clear from the results of the articles of Examples having the grip regions and the article of Comparative Example 2 in which no grip region is present that the articles of the invention are excellent in terms of operational performance (gripping performance). Moreover, from the results of the articles of Examples using the cloth support as the support and the article of Comparative Example 3 using the film as the support, the articles of the invention have characteristics that are excellent in respect of deviated rolling, unrolling, and operational performance (adhesiveness).

As described above, since the temporary attachment layer is provided at the interface between the back face of the cloth support and the back face of the release liner in the roll body obtained by rolling the band-like patch including the cloth support, the pressure-sensitive adhesive layer, and the release liner, rolling can be suitably made without causing deviated rolling or unrolling. Additionally, since the temporary attachment region having the temporary attachment layer and the grip regions having no temporary attachment layer are present at the interface between the back face of the cloth support and the back face of the release liner, the patch can be simply and easily pulled out by gripping the grip regions with a person's hand or fingers.

When the band-like patch is rolled, the finishing end edge can be simply and easily fixed via the second temporary attachment layer formed on the back face of the release liner or the back face of the cloth support that constitutes the band-like patch.

Additionally, when the band-like patch is rolled around the rolling core, the starting end edge of the band-like patch can be simply and easily fixed to and rapidly rolled around the rolling core, and it is possible to be favorably used as a roll body of a band-like patch with no deformation (unwanted appearance) caused by the bonding layer and with pleasing appearance even if the band-like patch is rolled around the rolling core.

While the invention has been described in detail and with reference to specific embodiments thereof, it will be apparent to one skilled in the art that various changes and modifications can be made therein without departing from the scope thereof.

This application is based on Japanese patent application No. 2011-168470 filed Aug. 1, 2011, Japanese utility model application No. 2011-000114 filed Jan. 12, 2012 and Japanese patent application No. 2012-035590 filed Feb. 21, 2012, the entire contents thereof being hereby incorporated by reference.

DESCRIPTION OF REFERENCE NUMERALS AND SIGNS

1: ROLL BODY OF BAND-LIKE PATCH
2: BAND-LIKE PATCH

3: FINISHING END EDGE
4: ROLLING CORE
5: STARTING END EDGE
11: TEMPORARY ATTACHMENT LAYER (TEMPORARY ATTACHMENT REGION)
12: GRIP REGION
13: RELEASE LINER
14: PRESSURE-SENSITIVE ADHESIVE LAYER
15: CLOTH SUPPORT
16: BONDING LAYER
21, 22: BOTH WIDTH END EDGES
23, 24: BOTH END CORNERS OF FINISHING END EDGE
25, 26, 27: SECOND TEMPORARY ATTACHMENT LAYER

What is claimed is:

1. A roll body of a patch formed by rolling a patch comprising a cloth support, a pressure-sensitive adhesive layer, and a release liner laminated in this order,
wherein at least one temporary attachment region in which a temporary attachment layer is formed and at least one grip region in which the temporary attachment layer is not formed are provided between a surface of the release liner opposite to the pressure-sensitive adhesive layer laminated surface and a surface of the cloth support opposite to the pressure-sensitive adhesive layer laminated surface; and
wherein the surface of the release liner opposite to the pressure-sensitive adhesive layer laminated surface and the surface of the cloth support opposite to the pressure-sensitive adhesive layer laminated surface are directly attached to each other via the temporary attachment layer in the roll body of the patch.

2. The roll body of a patch according to claim 1,
wherein said temporary attachment region in which the temporary attachment layer is formed and said grip region in which no temporary attachment layer is formed are provided on the surface of the release liner opposite to the pressure-sensitive adhesive layer laminated surface.

3. The roll body of a patch according to claim 1,
wherein said grip regions are located at both width end edges of the patch.

4. The roll body of a patch according to claim 1,
wherein said grip region is located at a finishing end edge of the patch.

5. The roll body of a patch according to claim 1,
wherein said temporary attachment layer exposed after pulling out the patch from the roll body has substantially no surface tackiness.

6. The roll body of a patch according to claim 1,
wherein said temporary attachment layer is constituted of a hot melt material.

7. The roll body of a patch according to claim 1,
wherein a shape of said temporary attachment layer is dotted, grid-like, or linear along the longitudinal direction of the patch.

8. The roll body of a patch according to claim 1,
wherein said temporary attachment region is substantially line-symmetric with respect to the center of width of the patch.

9. The roll body of a patch according to claim 1, further comprising a rolling core around which the patch is rolled, and a bonding layer provided between the rolling core and the patch.

10. The roll body of a patch according to claim 9,
wherein a planar shape of the bonding layer is a substantially rectangular shape formed by a length (W) of the bonding layer in the width direction of the surface of the rolling core and a length (L) of the bonding layer in the rolling direction of the surface of the rolling core, and
wherein a length (W) of the bonding layer in the width direction of the surface of the rolling core is a length that is 50% to 100% of a total width (W0) of the surface of the rolling core, and a length (L) of the bonding layer in the rolling direction of the surface of the rolling core is a length that is 3 mm or more and that is 1 to 100% of a total circumferential length (L0) of the surface of the rolling core in the rolling direction.

* * * * *